United States Patent [19]

Iwamura

[11] Patent Number: 4,548,831

[45] Date of Patent: Oct. 22, 1985

[54] ACID AND ALKALI INSOLUBLE FOOD COMPONENT FROM LEGUMINOUS PLANTS

[75] Inventor: Junichi Iwamura, Kashiwara, Japan

[73] Assignee: Tokiwa Kanpo Pharmaceutical Co., Ltd., Osaka, Japan

[21] Appl. No.: 545,577

[22] Filed: Oct. 26, 1983

[30] Foreign Application Priority Data

Dec. 17, 1982 [JP] Japan .................................. 57-22287

[51] Int. Cl.$^4$ ............................................... A23L 1/20
[52] U.S. Cl. ................................... 426/634; 426/656; 426/658; 426/431; 426/481
[58] Field of Search ................ 426/632, 634, 656, 658

[56] References Cited

U.S. PATENT DOCUMENTS 3,261,822  7/1966  Robbins et al. .................. 426/632 X
4,309,344  1/1982  Walsh .............................. 426/634 X
4,410,554  10/1983 Sailer .............................. 426/634 X

FOREIGN PATENT DOCUMENTS 2039204  8/1980  United Kingdom .

Primary Examiner—Robert Yoncoskie

[57] ABSTRACT

A health food comprising acid- and alkali-insoluble substances obtained as an unextractable residue on extracting defatted seeds of leguminous plants with acid and alkali. Said health food is useful in prophylactic and therapeutic treatment of obesity.

2 Claims, No Drawings

ACID AND ALKALI INSOLUBLE FOOD COMPONENT FROM LEGUMINOUS PLANTS

The present invention relates to a health food which is useful in prophylactic and therapeutic treatment (dietotherapy) of obesity.

Recently, increase of obesity caused by superalimentation is attracting a social interest. Such an obesity is liable to cause acceleration of arteriosclerosis and fatty liver, onset of maturity diabetes, coronary sclerosis, degenerative joint disease etc. by increase in cholesterol level in serum and liver. Accordingly, it is essential for those who have an inclination to grown fat, to monitor the change of body weight of themselves and to effect for prophylaxis and early treatment of obesity.

The most common and conventional treatment of obesity is a hunger cure. However, this pains patients and can not be easily realized. More recently, there have been marketed formulations to be taken with a view of prophylaxis and treatment of obesity, so-called a 'fat-reducers', most of which, however, contain an ingredient having toxicity, such as enzyme inhibitory action, which may soil good health and hence are not perfect.

As a result of an extensive study searching for a food which is useful in dietotherapy of obesity and has not substantially undesirable side-effect, it has now been discovered that a food usable for preventing obesity can be obtained from seeds of leguminous plants, quite unexpectedly in view of fact that the seeds of leguminous plants generally have high nutritive values. More particularly, it has been discovered that acid- and alkali-insoluble matters obtained by treating defatted seeds of leguminous plants such as a defatted soybean cake with acid and alkali are indigestible, have not any undesirable side effect and hence be used as a food for preventing obesity. The present invention has been completed on the basis of the above discovery.

According to the invention, there is provided a health food comprising acid- and alkali-insoluble substances obtained as an unextractable residue on extracting defatted seeds of leguminous plants with acid and alkali.

The defatted seeds of leguminous plants used in the invention include seeds of plants belonging to Leguminosae, which are used commonly for foods or drugs and which are pre-defatted. Typical examples for these seeds are soybeans, black-soybeans, broad beans, peas, red beans, peanuts, seeds of Cassia tora and seeds of *Cassia obtusifolia* (Cassia Seed). The defatting may be carried out ordinarily in the following manner. Seeds are crushed into appropriate sizes (ordinarily about 1/16–⅛) and optionally separated from seed coat. The crushed seeds are treated with heat at 100°–130° C. in order to coagulate protein and then rolled using rollers (usually corrugated roller mill). The rolled pieces are extracted with nonpolar organic solvent (for example, petrolic solvent such as petroleum ether, n-hexane etc. or other solvents for defatting). The extracting is ordinarily carried out under heating at around 50° C. The extract is evaporated to recover oil.

The health food according to the invention is obtained as a residue on extracting the defatted seeds of leguminous plants as in the above described manner with acid and alkali. The extraction may be carried out with whichever one of acid or alkali before with the other, however, the alkali extraction normally goes first. A diluted aqueous solution (normally not more than 1%) of sodium hydroxide, potassium carbonate etc. can be used for the alkali extraction, through which water soluble proteins are removed. The acid extraction can be carried out with a diluted aqueous solution (normally about pH 5) of a mineral or organic acid, preferably an organic acid such as acetic acid, propionic acid etc. In either cases, suitable extracting temperature is around the room temperature. After the extraction, the residue is washed sufficiently with water and dried. Although air drying may be applied, the more preferred is vacuum drying or lyophilization, because the residue is liable to be colored in the course of air drying.

The obtained acid- and alkali-insoluble substances comprise fibrous materials. These can be used as the health food according to the invention either as such or as a formulation commonly used as an internal medicine, such as tablets, pills, granules, powders, capsules etc., prepared by powdering the substances and if necessary admixing with excipient. Alternatively, the substances may be mixed in food s such as yogurts, candies, cookies, jellies, etc. Further, the health food of the invention may be mixed with other pharmaceuticals, herb medicines etc.

The health food according to the invention exhibit adiposity-preventing activity and inhibit increase in body weight when it is taken in. The health food of the invention, therefore, has effect on prophylaxis and therapy of adult diseases such as arteriosclerosis, fatty liver, diabetes, rectal carcinoma etc. and maintenance or recovery of health.

The effect of the health food according to the invention is indicated by the following tests.

TEST 1.

Effect on Body Weight (1) Route for medication: per os.
(2) Animals used: dd Y-N strain, male mice. Week of age and initial body weight: about 5 weeks, male 20 g.
(3) Room temperature: 22±2° C.
(4) Preparation of test liquid: Test liquid was prepared by finely dividing specimen, suspending 20 g of the divided specimen in distilled water to make 100 ml of suspension (20% suspension of the specimen).
(5) Method of administration of the test liquid etc.
 (a) Method of administration; The test liquid was perorally administered once by forced feeding through stomach tube.
 (b) Number of animals per a test group; Male, each 10 animals.
(6) Weighing of body weight: 7 days after.
(7) Test results:

| Dosage | Mouse No. | Initial Body Weight (g) | Final Body Weight (g) | Dosage | Mouse No. | Initial Body Weight (g) | Final Body Weight (g) |
|---|---|---|---|---|---|---|---|
| 6,900 mg/kg | 1 | 20 | 24 | 10,000 mg/kg | 21 | 20 | 23 |
| | 2 | 20 | 25 | | 22 | 20 | 24 |
| | 3 | 20 | 26 | | 23 | 20 | 25 |
| | 4 | 20 | 27 | | 24 | 20 | 25 |
| | 5 | 20 | 28 | | 25 | 20 | 26 |
| | 6 | 20 | 25 | | 26 | 20 | 25 |
| | 7 | 20 | 28 | | 27 | 20 | 26 |
| | 8 | 20 | 29 | | 28 | 20 | 26 |
| | mean | 20.0 | 26.5 | | mean | 20.0 | 25.0 |
| 8,300 mg/kg | 11 | 20 | 22 | 12,000 mg/kg | 31 | 20 | 24 |
| | 12 | 20 | 22 | | 32 | 20 | 25 |
| | 13 | 20 | 24 | | 33 | 20 | 25 |
| | 14 | 20 | 25 | | 34 | 20 | 25 |

-continued

| Dosage | Mouse No. | Initial Body Weight (g) | Final Body Weight (g) | Dosage | Mouse No. | Initial Body Weight (g) | Final Body Weight (g) |
| --- | --- | --- | --- | --- | --- | --- | --- |
| | 15 | 20 | 25 | | 35 | 20 | 28 |
| | 16 | 20 | 23 | | 36 | 20 | 23 |
| | 17 | 20 | 24 | | 37 | 20 | 26 |
| | 18 | 20 | 25 | | 38 | 20 | 26 |
| | mean | 20.0 | 23.8 | | mean | 20.0 | 25.3 |
| control | | | | 0 mg/kg | | 20.0 | 27.5 |

It can be clearly seen from the above test result that increase in the body weight is prevented by only once administration when dosage reaches to an amount of 6,900 mg/kg to 8,300 mg/kg or more.

TEST 2

Acute Toxicity (1) Route for medication: per os.
(2) Animals used: dd Y-N strain, male and female. Week of age and initial body weight: about 5 weeks, male 20-22 g, female 18-20 g.
(3) Room temperature: 22±2° C.
(4) Preparation of test liquid: Test liquid was prepared by finely dividing specimen, suspending 20 g of the divided specimen in distilled water to make 100 ml of suspension (20% suspension of the specimen).
(5) Method of administration of the test liquid etc.
   (a) Method of administration; The test liquid was perorally administered once by forced feeding through stomach tube.
   (b) Calcuration of $LD_{50}$: Probit method.
   (c) Concentration ratio of specimen given: 1:1.2.
   (d) Number of animals per a test group: each 10 animals for male and female.
(6) Test result:

| Sex | Group No. | Dosage (mg/kg) | Mortality with passage of time (hrs) 5 | (hrs) 15 | (days) 1 2 3 4 5 6 7 | Mortality (%) | $LD_{50}$ (mg/kg) |
| --- | --- | --- | --- | --- | --- | --- | --- |
| male | 1 | 6,900 | 0/10 | 0/10 | 0/10→0/10 | 0 | >12,000 |
| | 2 | 8,300 | 0/10 | 0/10 | 0/10→0/10 | 0 | |
| | 3 | 10,000 | 0/10 | 0/10 | 0/10→0/10 | 0 | |
| | 4 | 12,000 | 0/10 | 0/10 | 0/10→0/10 | 0 | |
| female | 1 | 6,900 | 0/10 | 0/10 | 0/10→0/10 | 0 | >12,000 |
| | 2 | 8,300 | 0/10 | 0/10 | 0/10→0/10 | 0 | |
| | 3 | 10,000 | 0/10 | 0/10 | 0/10→0/10 | 0 | |
| | 4 | 12,000 | 0/10 | 0/10 | 0/10→0/10 | 0 | |

(7) Toxic symptoms: No disorder was observed in both male and female groups from immediately after the administration and growth was seemed to be normal afterwards.
(8) Findings on autopsy: Abnormality was not observed in main internal organs.
(9) Consideration: No mortal case was found in both male and female groups even at a dosage of 12,000 mg specimen/Kg in this test.

The dosage of 12,000 mg/Kg corresponds to administration dosage of 60 ml/Kg which was considered to be the upper limit of once peroral administration dosage of the test liquid to mouse. Concentration of 20% was considered to be the maximum concentration administrable through stomach tube due to the swelling of the specimen when suspended in water. Accordingly, it was concluded that the peroral $LD_{50}$ of the specimen was more than 12,000 mg/Kg for both male and female groups.

It can be safely said that the health food according to the invention has an extremely low toxicity.

The following examples illustrate the invention.

EXAMPLE 1

To 1 part of defatted soybean (extracting solvent: n-hexane) were added 7-15 parts of 4% aqueous sodium hydroxide solution and the mixture was stirred at room temperature for 1-1.5 hours. Solid substances were collected by filtration or centrifugation and 7-15 parts of water were added to them. The mixture was adjusted to pH 5 with acetic acid and stirred at room temperature for 10-20 minutes. Precipitates of proteins formed in acidic medium were removed using a net of 12-36 mesh and fibrous extraction residue was washed sufficiently with water. Then water was removed by filtration under pressure or centrifugation and the residue was dried at low temperature under reduced pressure to give health food of the invention (yield 26.3-38.2%).

Analytical result of the product are as follows:

| Proteins (factor 5.71) | 31.4% |
| --- | --- |
| Fibers | 18.4% |
| Ash | 5.4% |
| Total pectin[1] | 5.34% |
| Cellulose[2] | 25.5% |
| Calcium | 1.24% |
| Potassium | 195 mg/100 g |
| Iron | 64.9 mg |

Note
[1] by carbazol colorimetry (as galacturonic acid)
[2] by the method of P. J. Van Soest The health food according to the invention was also obtained by treating defatted black soybeans or defatted peanuts in a manner similar to the above description.

EXAMPLE 2

| health food obtained in Example 1 | 150 parts |
| --- | --- |
| lactose | 90 parts |

The above ingredients were mixed and introduced into a hard-shell gelatin capsule.

EXAMPLE 3

| health food obtained in Example 1 | 80 parts |
| --- | --- |
| wheat flour | 100 parts |
| shortening | 15 parts |
| sugar | 13 parts |
| condensed milk | 6 parts |
| refined sugar | 18 parts |
| sodium hydrogen carbonate | 0.6 parts |
| butter | 10 parts |
| water | 6 parts |

The above ingredients were mixed and baked into a biscuit.

What is claimed is:

1. A health food comprising acid- and alkali-insoluble substances obtained as an unextractable residue on extracting defatted seed of leguminous plants first with alkali and then with acid.

2. A health food as recited in claim 1 wherein the acid extraction is carried out utilizing an acid selected from the group consisting of acetic acid and propionic acid.

* * * * *